United States Patent [19]
Alfano et al.

[11] Patent Number: 5,635,402
[45] Date of Patent: Jun. 3, 1997

[54] TECHNIQUE FOR DETERMINING WHETHER A CELL IS MALIGNANT AS OPPOSED TO NON-MALIGNANT USING EXTRINSIC FLUORESCENCE SPECTROSCOPY

[76] Inventors: Robert R. Alfano, 3777 Independence Ave., Bronx, N.Y. 10463; Cheng H. Liu, 140-25 Ash Ave. Apt. #3A, Flushing, N.Y. 11355; Wei L. Sha, 501 W. 147th St., Apt. #3C, New York, N.Y. 10031; Yury Budansky, 736 Ramapo Valley Rd., Oakland, N.J. 07436

[21] Appl. No.: 236,861

[22] Filed: Apr. 29, 1994

Related U.S. Application Data

[63] Continuation of Ser. No. 845,928, Mar. 5, 1992, abandoned.

[51] Int. Cl.⁶ .................. G01N 21/64; G01N 33/52
[52] U.S. Cl. .................. 436/63; 436/64; 436/172; 250/459.1; 250/461.2
[58] Field of Search .................. 436/63–64, 172, 436/800, 813, 149, 811; 250/461.2, 459.1

[56] References Cited

U.S. PATENT DOCUMENTS

| | | | |
|---|---|---|---|
| 4,424,201 | 1/1984 | Valinsky et al. | 436/800 |
| 4,696,905 | 9/1987 | Aoyama et al. | 436/64 |
| 4,741,043 | 4/1988 | Bacus | 382/6 |
| 4,773,097 | 9/1988 | Suzaki et al. | 250/461.2 |
| 4,778,763 | 10/1988 | Makiguchi et al. | 436/172 |
| 4,782,015 | 11/1988 | Allison et al. | 435/7 |
| 4,930,516 | 6/1990 | Alfano et al. | 128/665 |
| 4,954,435 | 9/1990 | Krauth | 436/811 |
| 4,957,114 | 9/1990 | Zeng et al. | 128/665 |
| 5,042,494 | 8/1991 | Alfano | 128/665 |
| 5,199,431 | 4/1993 | Kittrell et al. | |

FOREIGN PATENT DOCUMENTS 2-22331  7/1983  Japan .

OTHER PUBLICATIONS

Steven et al., Anticancer Res., (1992, Nov.–Dec.) 12 (6B) pp. 2147–2149.
Berns et al. Lasers Surg. Med (1983) 2(3) 261–6.
G. Tang et al., Applied Optics, vol. 28, No. 12, pp. 2337–2342 (1989).
F. Khanum et al., Photochemistry and Photobiology, vol. 50, No. 5, pp. 647–651 (1989).
R. Alfano et al., IEEE Journal of Quantum Electronics, vol. QE-23, No. 10, pp. 1806–1811 (1987).
G. Bottiroli et al., Photochemistry and Photobiology, vol. 46, No. 5, pp. 663–667 (1987).
J. Evensen et al., Photochemistry and Photobiology, vol. 46, No. 5, No. 5, pp. 859–865 (1987).
H. Schneckenburger et al., Photochemistry and Photobiology, vol. 46, No. 5, pp. 765–768 (1987).
R. Baumgartner et al., Photochemistry and Photobiology, vol. 46, No. 5 pp. 759–763 (1987).

(List continued on next page.)

*Primary Examiner*—Jeffrey Snay
*Attorney, Agent, or Firm*—Kriegsman & Kriegsman

[57] ABSTRACT

A technique for determining whether a cell is malignant as opposed to non-malignant using extrinsic fluorescence spectroscopy. The technique is premised on the principle that certain fluorescent dyes preferentially stain malignant cells as opposed to non-malignant cells. Accordingly, by exposing a cell to the fluorescent dye, irradiating the cell with light of such a wavelength as to cause the dye to fluoresce, measuring the intensity of fluorescence at a wavelength indicative of fluorescence of the dye, and comparing the fluorescence intensity to standards obtained from malignant cells and non-malignant cells, it is possible for one to accurately classify the cell as being either malignant or non-malignant. The present invention also relates to an automated system which applies the principles of the aforementioned technique to depict the spatial distribution of cells within an area of a Pap smear-type sample and to characterize each of the cells as being malignant or non-malignant.

25 Claims, 9 Drawing Sheets

OTHER PUBLICATIONS

L. Cincotta et al., Photochemistry and Photobiology, vol. 46, No. 5, pp. 751–758 (1987).

J. Moan et al., Photochemistry and Photobiology, vol.. 46, No. 5, pp. 713–721 (1987).

G. Bertolini et al., Photochemistry and Photobiology, vol. 46, No. 5, pp. 695–698 (1987).

C. Milanesi et al., Photochemistry and Photobiology, vol. 46, No. 5, pp. 675–678 (1987).

R. Alfano et al., IEEE Journal of Quantum Electronics, vol. QE–20, No. 12, pp. 1507–1511 (1984).

J. Spears et al., J. Clin. Invest., vol. 71, pp. 395–399 (1983).

TECHNIQUE FOR DETERMINING WHETHER A CELL IS MALIGNANT AS OPPOSED TO NON-MALIGNANT USING EXTRINSIC FLUORESCENCE SPECTROSCOPY

This is a continuation of application Ser. No. 07/845,928 filed on Mar. 5, 1992, now abandoned.

BACKGROUND OF THE INVENTION

The present invention relates generally to techniques for detecting cancer and more particularly to a novel technique for determining whether a cell is malignant as opposed to non-malignant using extrinsic fluorescence spectroscopy.

Over the years, scientists have contributed to the many advances in our understanding of cancer. In 1775, Percivall Pott made his historic contribution to carcinogenesis when he described squamous cell carcinoma in chimney sweepers. Biopsies of cancer began to be accepted at the turn of the twentieth century. In 1895, Cullin described the frozen section technique, but it was not until the 1940's that pathological studies became accepted as a reliable way to diagnose malignancies. Cytology began in 1837 with Dunne's microscopic studies of body fluids. In 1847, Pouchet published the first study of the exfoliative cytology of the female genital tract. The first report of the usefulness of the smear technique as diagnostic aid in cancer of the cervix came with the work of George Papanicolaou (after whom the "Pap smear" test was named) in 1928. Cytological diagnoses for cancer of the stomach and respiratory tract were developed late in the 1950's and early in the 1960's.

Treatments for carcinomas of the vulva, vagina, and cervix have greatly improved in the twentieth century due to the combination of advances including wide cervical excisions, radiotherapy, both external beam and implants, and the early diagnosis of cancer using Pap smears. Typically, Pap smears are inspected visually using a microscope. Over the years, the large volume of slides being read has resulted in errors in diagnosis, the errors most frequently being attributed to human error in reading the slides or to a collection of smear deposited on the slides. Accordingly, there is a need to analyze Pap smears by other means. Presently, computer-VIDEO software programs are being investigated to compare cell patterns to recognize cancer cells from normal cells in shape and size.

SUMMARY OF THE INVENTION

It is an object of the present invention to provide a new technique for determining whether a cell is malignant as opposed to non-malignant.

The present invention is based on the principle that certain fluorescent dyes preferentially stain malignant cells as opposed to non-malignant cells. Using this principle, the present inventors have found that it is possible to determine whether a cell is malignant as opposed to non-malignant by exposing the cell to the fluorescent dye, exciting the cell with light or such a wavelength as to cause the dye to fluoresce, measuring the intensity of the resultant fluorescence at a wavelength indicative of fluorescence of the fluorescent dye, and comparing the intensity of the resultant fluorescence to standards obtained from malignant cells and non-malignant cells.

One application of the present invention resides in the creation of a "map" of an area of a stained Pap smear-type sample, such a "map" typically conveying information regarding the spatial distribution of cells within the area examined and a characterization of each cell within the area as being either malignant or non-malignant. In this way, the number of malignant cells and non-malignant within the examined area may be counted and compared to accepted values. According to the teachings of the present invention, such a map may be made using an automated system. In an exemplary embodiment, the automated system includes means for exciting an area of the Pap smear-type sample which has been stained with a fluorescent dye of the type described above with light of a wavelength sufficient to cause the fluorescent dye to fluoresce, a detector for converting light signals incident thereonto into corresponding electrical signals, optics for imaging the excited area of the Pap smear-type sample onto the detector, filter means disposed before the detector for selecting from the light signals emitted from the excited area of the Pap smear-type sample fluorescent light at a wavelength indicative of fluorescence of the fluorescent dye, processing means for comparing the intensity of each of the electrical signals emitted by the detector to standards for malignant and non-malignant cells and for creating a map conveying the spatial distribution of cells within the area excited and a characterization of each cell within the area excited as being either malignant or non-malignant, and display means for displaying the map.

One advantage to an automated system of the type described above is that it does not rely on a visual inspection of the cells by an operator. Accordingly, the skill of the operator and/or operator error is not a factor.

Another advantage to an automated system of the type described above is that it does not depend on subjective parameters of cell shape and/or cell size. Accordingly, such a system is expected to be inherently More accurate than existing techniques.

Additional objects, features, and advantages of the present invention will be set forth in part in the description which follows, and in part will be obvious from the description or may be learned by practice of the invention. The objects, features, and advantages of the present invention may be realized and attained by means of the instrumentalities and combinations particularly pointed out in the appended claims.

BRIEF DESCRIPTION OF THE DRAWINGS

The accompanying drawings, which are hereby incorporated into and constitute a part of this specification, illustrate the preferred embodiments of the invention and, together with the description, serve to explain the principles of the invention. In these drawings wherein like reference numerals represent like parts:

FIGS. 4(a) and 4(b) through 9(a) and 9(b) are schematic diagrams illustrating how dye-stained malignant and non-malignant cells can be distinguished by their respective fluorescence intensities profiles according to the teachings of the present invention;

DETAILED DESCRIPTION OF PREFERRED EMBODIMENTS

As discussed above, the present invention is directed to a novel technique for determining whether a cell is malignant as opposed to non-malignant. The present invention exploits the well-known fact that certain dyes, such as hematoporphyrin (HP), hematoporphyrin derivative (HPD), dihematoporphyrin ether/ester (DHE), tetramicin, rhodamine, cyanine, and others, preferentially stain malignant cells as opposed to non-malignant cells. Such dyes have typically been used in the past as photosensitizers used in the treatment of cancer. Typically, such dyes are administered to a patient having a malignancy. After a period of time, the dyes preferentially bind to malignant cells. Intense light, typically in the form of laser light, is then used to kill the malignant cells which have taken up the dyes.

While having been used in the past to kill malignant cells, such dyes have not been used in the past to determine the presence of malignant cells. By way of contrast, the present invention provides such a method for determining the presence of malignant cells. According to the teachings of the present invention, a fluorescent dye having a preference for staining malignant cells as opposed to non-malignant cells is added to a cell whose condition is unknown. Next, the cell is irradiated with light of a wavelength sufficient to cause the fluorescent dye to fluoresce. The intensity of fluorescence at a wavelength indicative of fluorescence of the dye is then measured and compared to standards obtained from malignant cells and non-malignant cells. Typically, the intensity of fluorescence from malignant cells is higher than that from non-malignant cells because malignant cells have a higher affinity for the fluorescent dye than do non-malignant cells.

As mentioned above, the novel technique of the present invention for distinguishing malignant cells from non-malignant cells can be applied, amongst other things, to the automated screening of Pap smear-type samples. In one embodiment, such screening may involve creating a map of the cells located within an area of the sample, the map depicting the spatial distribution of cells within the area and information as to whether each cell is malignant or non-malignant. In this way, the number of malignant and non-malignant cells can be counted, and the sample may be graded according to well-known standards.

Figure 1:
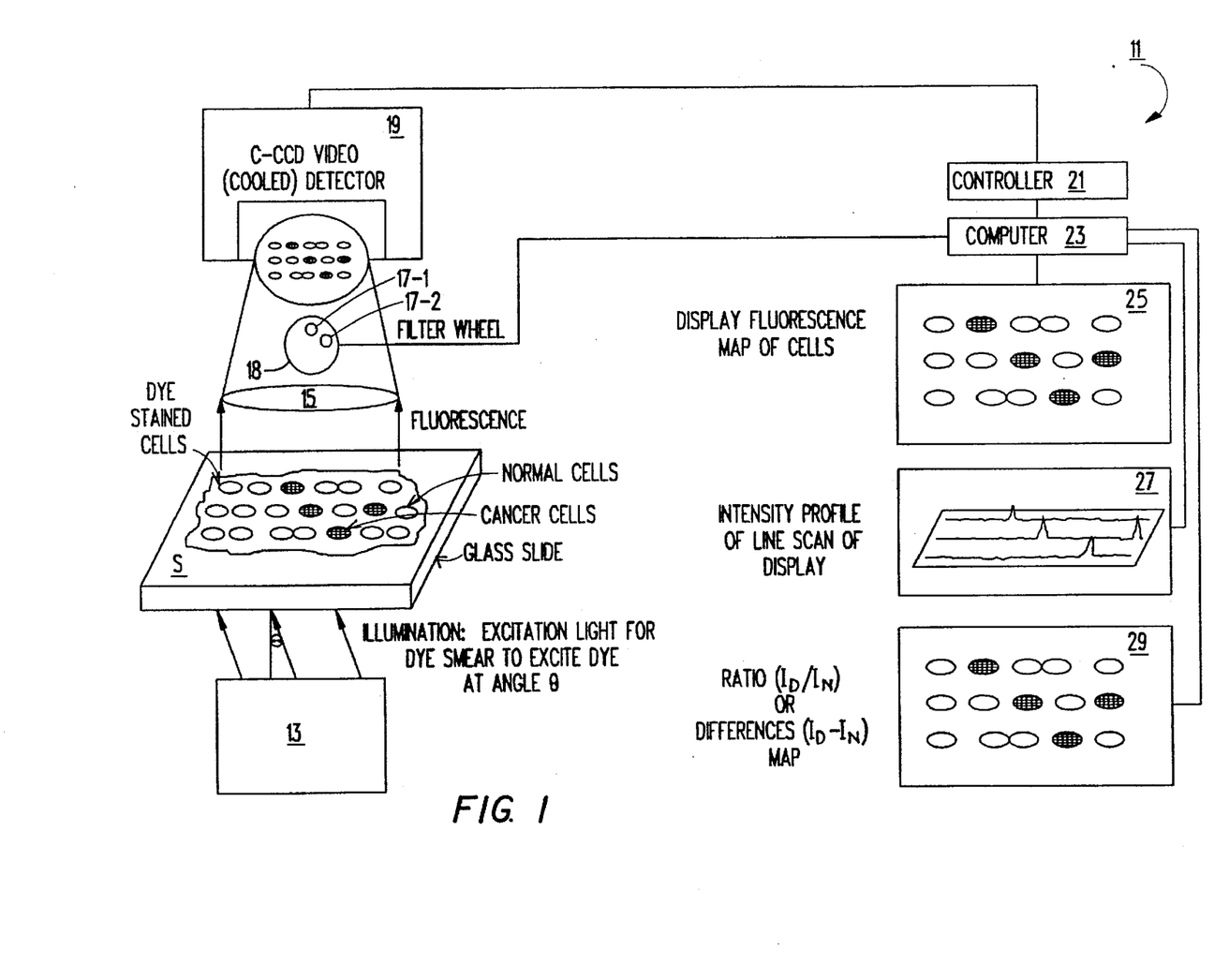
FIG. 1 is a schematic diagram of one embodiment of a system constructed according to the teachings of the present invention for making a map of the cells located within an area of a Pap smear-type sample, the map conveying the spatial distribution of cells within the area and a characterization of each of the cells as being either malignant or non-malignant.

Referring now to FIG. 1, there is illustrated one embodiment of a system constructed according to the teachings of the present invention for making a map of the type described above, the system being represented by reference numeral 11.

System 11 includes a light source 13 for illuminating a Pap smear-type sample S, to which a fluorescent dye has been added which preferentially stains malignant as opposed non-malignant cells, at a wavelength appropriate to excite the fluorescent dye, i.e., at a wavelength within the absorption curve for the dye. The light produced by light source 13 is typically either in the form of a continuous beam of light or pulses of sufficiently long duration to minimize the effects of time-resolved fluorescence for the period over which fluorescence is measured. Preferably, light source 13 is a laser system or lamp capable of producing light at multiple wavelengths. Where the fluorescent dye used to stain the cells in the sample is selected from the group consisting of hematoporphyrin (HP), hematoporphyrin derivative (HPD), or dihematoporphyrin ether/ester (DHE), the light generated by light source 13 typically has a wavelength in the range from about 300 nm to about 600 am, preferably from about 300 nm to about 400 nm, more preferably from about 350 nm to about 400 nm.

An area of the sample S is focused by optics 15, which may be a lens, microscope, or other magnification means, and the fluorescence emitted from the area is passed through one of two filters 17-1 and 17-2 mounted on a rotatably adjustable, computer-controlled filter wheel 18. One filter 17-1 of filter wheel 18 is selective for light having a wavelength ($\lambda$hd D) that is characteristic of fluorescence for the type of dye used to stain tile cells in sample S. The other filter 17-2 of filter wheel 18 is selective for light having a wavelength ($\lambda_N$) that is characteristic of native fluorescence for the cells in sample S. If HPD or DHE is the fluorescent dye used, filter 17-1 is preferably selective for light having a wavelength of about 630 nm or about 690 nm (i.e., the characteristic peak fluorescence intensities for HPD and DHE), and If HP is the fluorescent dye used, filter 17-1 is preferably selective for light having a wavelength of about 620 nm or about 660 nm (i.e., the characteristic peak fluorescence intensities for HP). In both cases, filter 17-2 is preferably selective for light having a wavelength of about 440 nm, about 560 nm, or about 580 nm (it being understood that the wavelength of the light selected by filter 17-2 must be longer than the wavelength of light generated by source 13; consequently, if the excitation wavelength is, for example, as great as 600 nm, filter 17-2 must be selective for native fluorescent light having a wavelength greater than 600 nm.) As can be seen, filter wheel 28 is designed so that the light emitted from the sample is caused to pass through filter 17-1 for one period of time and is then caused to pass through filter 17-2 for a successive period of time.

The filtered fluorescent light passing through either filter 17-1 or filter 17-2 then impinges on a detector 19, which converts the incident light into corresponding electrical signals. Detector 19 may be, for example, a C-CCD VIDEO detector, a SIT camera, an image intensified CCD or the like.

The signals from detector 19 are first transmitted to a controller 21 and are then transmitted to a computer 23 for processing. Using software, computer 23 then takes the fluorescence readings measured at wavelength $\lambda_D$, characterizes the source of the fluorescence as being either a malignant cell, a non-malignant cell, or background, and generates a map which depicts both spatially and graphically the source of the fluorescence. In characterizing the source of the fluorescence, the intensities of the fluorescence readings are typically compared to two types of distinguishing levels. The first level is a base level which is used to distinguish fluorescence derived from a malignant or non-malignant cell with fluorescence caused by background. The second level is a discriminator level which is used to distinguish between fluorescence derived from a malignant cell from fluorescence derived from a non-malignant cell. In comparing the intensities of the readings to the two types of levels as discussed above, the integrated area of a peak is typically used. The results generated by computer 23 are then displayed on a monitor or on hard copy as a map 25. As can be seen in the map shown in FIG. 1, four malignant cells are shown as dark ovals and eleven non-malignant cells are shown as light ovals.

As can well be appreciated, in addition to generating map 25, computer 23 can also be used to display the fluorescence readings at wavelength $\lambda_D$ in the form of a series of intensity profiles 27 corresponding to linear scans of map 25. Alternatively, using fluorescence readings both at wavelength $\lambda_D$ and at wavelength $\lambda_N$ computer 23 can generate a ratio (or differences) map 29 analogous to map 25.

Figure 2:
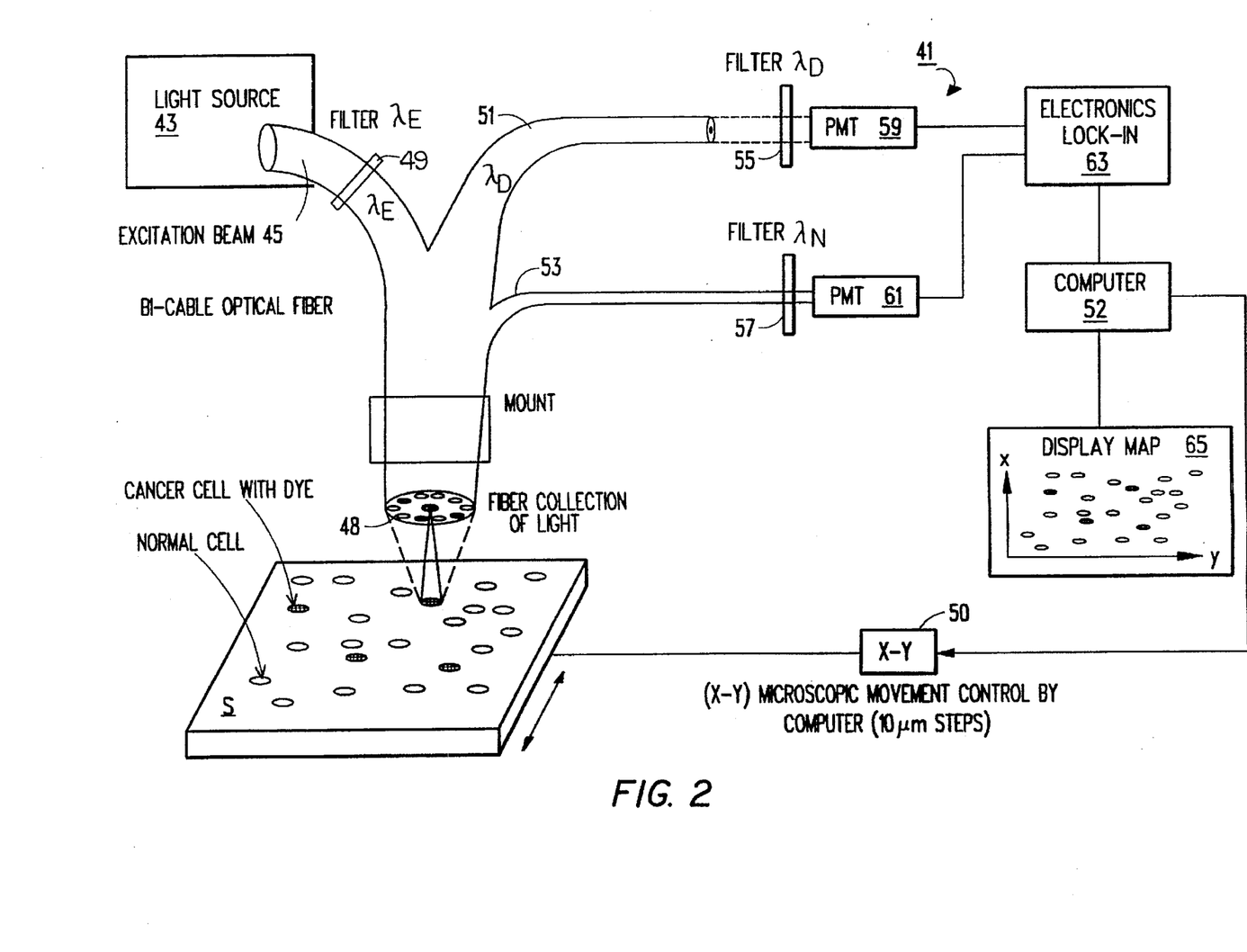
FIG. 2 is a schematic diagram of a second embodiment of a system constructed according to the teachings of the present invention for making a map of the cells located within an area of a Pap smear-type sample, the map conveying the spatial distribution of cells within the area and a characterization of each of the cells as being either malignant or non-malignant.

Referring now to FIG. 2, there is illustrated a second embodiment of a system constructed according to the teachings of the present invention for making a map of an area of a Pap smear-type sample, the system being represented by reference numeral 41.

System 41 includes a light source 43 for producing a beam of light to illuminate the Pap smear-type sample S. Light source 43 may be similar in construction to light source 13 of system 11. The light transmitted from light source 43 is sent through a first leg 45 of a trifurcated fiber optic bundle 47. Disposed within first leg 45 is a filter 49, which is selective for light of a wavelength which will cause the dye in the sample to fluoresce, i.e. at a wavelength within the absorption curve for the dye. Where the fluorescent dye used to stain the cells in the sample is selected from the group consisting of hematoporphyrin (HP), hematoporphyrin derivative (HPD), or dihematoporphyrin ether/ester (DHE), filter 49 is typically selective for light having a wavelength in the range from about 300 nm to about 600 nm, preferably from about 300 nm to about 400 nm, more preferably from about 350 nm to about 400 nm.

The light emergent from the probe end 48 of bundle 47 illuminates a small portion of the slide S upon which the sample is smeared. X-Y movement of slide S to permit scanning of a larger area of the sample is effected by a motorized device 50, which is controlled by a computer 52.

The light emitted from slide S is collected by probe end 48 of bundle 47 and then transmitted to a second leg 51 and a third leg 53 of bundle 47. Second leg 51 and third leg 53 of bundle 47 are equipped with filters 55 and 57, respectively, which function in the same manner as filters 17-1 and 17-2, respectively, of system 11.

The light passing through filters 55 and 57 is detected by photomultiplier tubes 59 and 61, respectively, and converted into electrical signals, which are transmitted to electronics lock-in 63 and then processed by computer 52. Computer 52 calculates either a ratio or a difference for each set of intensity readings at wavelengths $\lambda_D$ and $\lambda_N$ compares the results to standards, and displays the results on a display 65 in the form of a map with dark ovals indicating the presence of malignant cells and light ovals indicating the presence of non-malignant cells.

Figure 3:
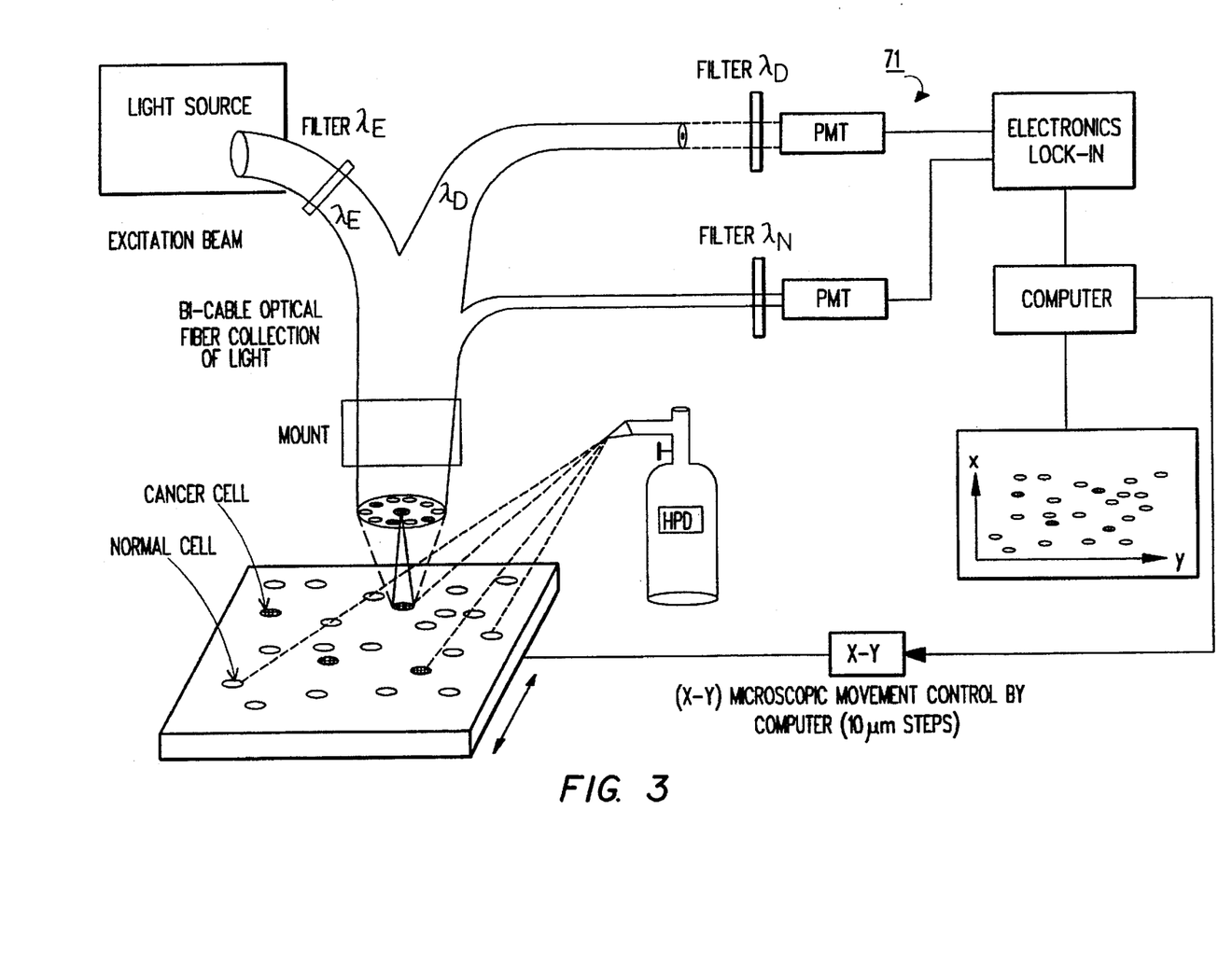
FIG. 3 is a schematic diagram of a third embodiment of a system constructed according to the teachings of the present invention for making a map of the cells located within an area of a Pap smear-type sample, the map conveying the spatial distribution of cells within the area and a characterization of each of the cells as being either malignant or non-malignant.
Figure 4A:
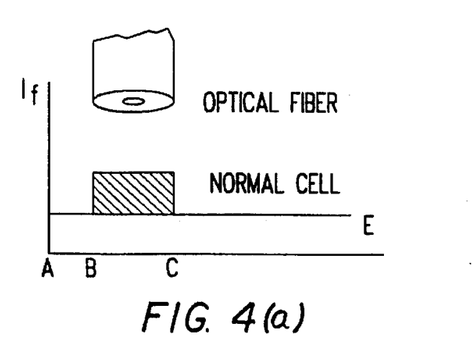
Figure 4B:
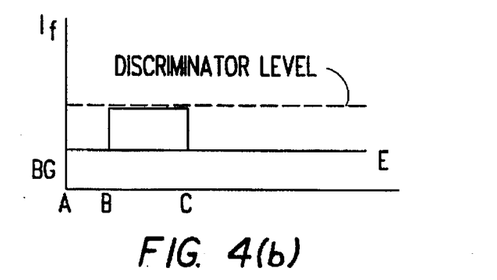
Figure 5A:
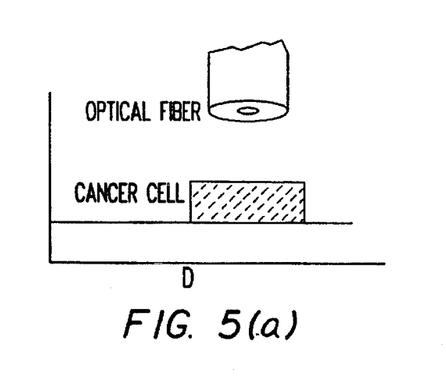
Figure 5B:
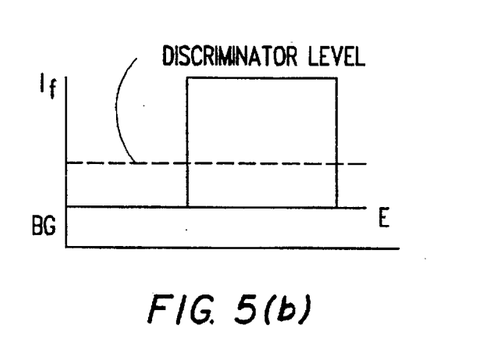
Figure 6A:
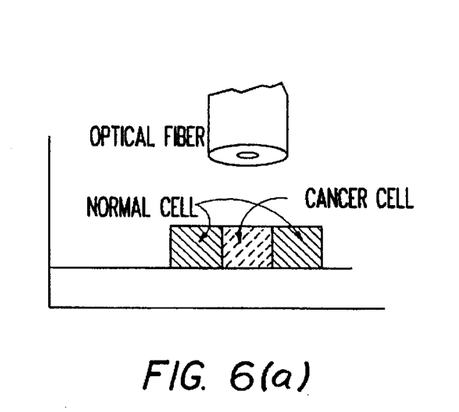
Figure 6B:
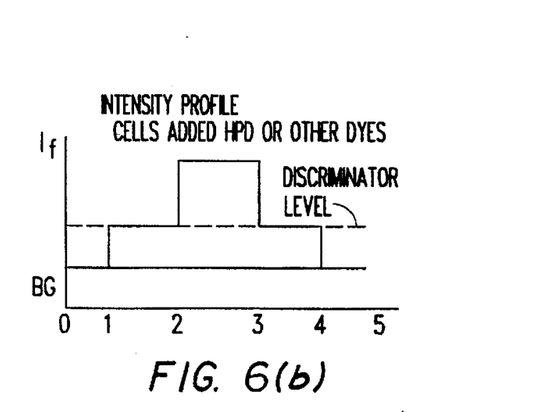
Figures 7A, 8A, 9A:
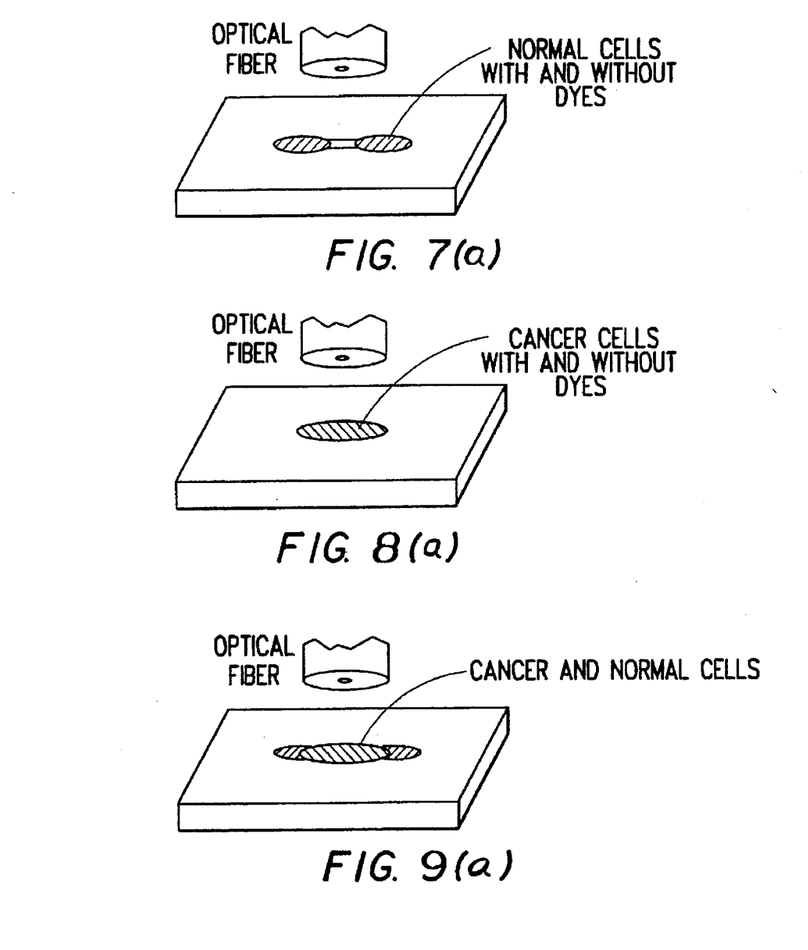
Figure 7B:
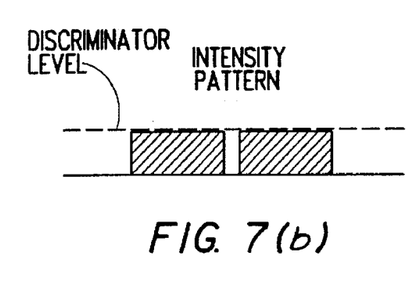
Figure 8B:
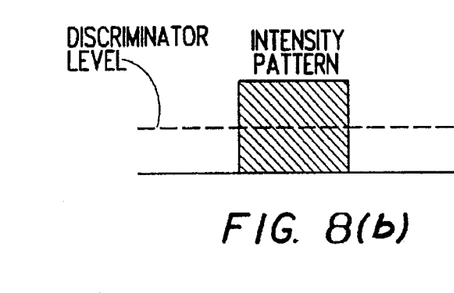
Figure 9B:
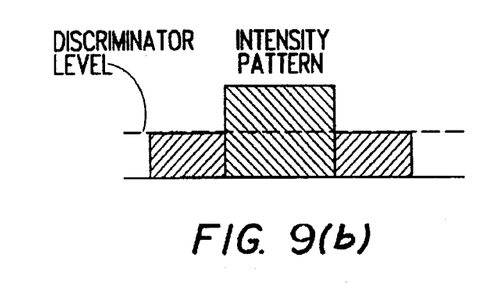
Figure 10A:
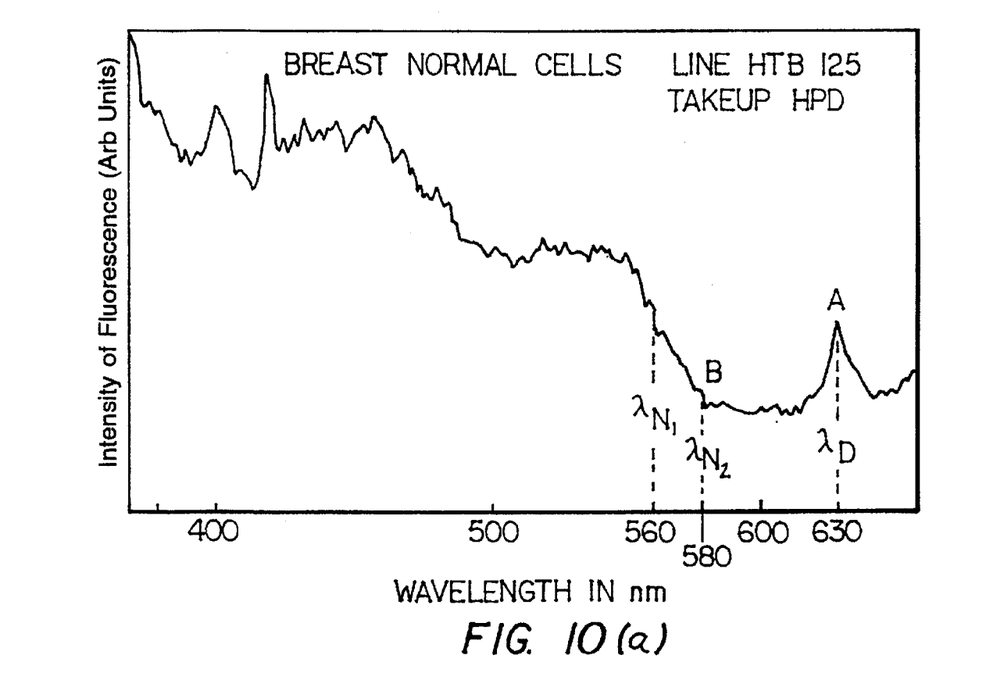
FIGS. 10(a) and 10(b) are the fluorescence emission spectra obtained when light at a wavelength of about 350 nm was used to excite normal cells to which hematoporphyrin derivative either was or was not added, respectively.
Figure 10B:
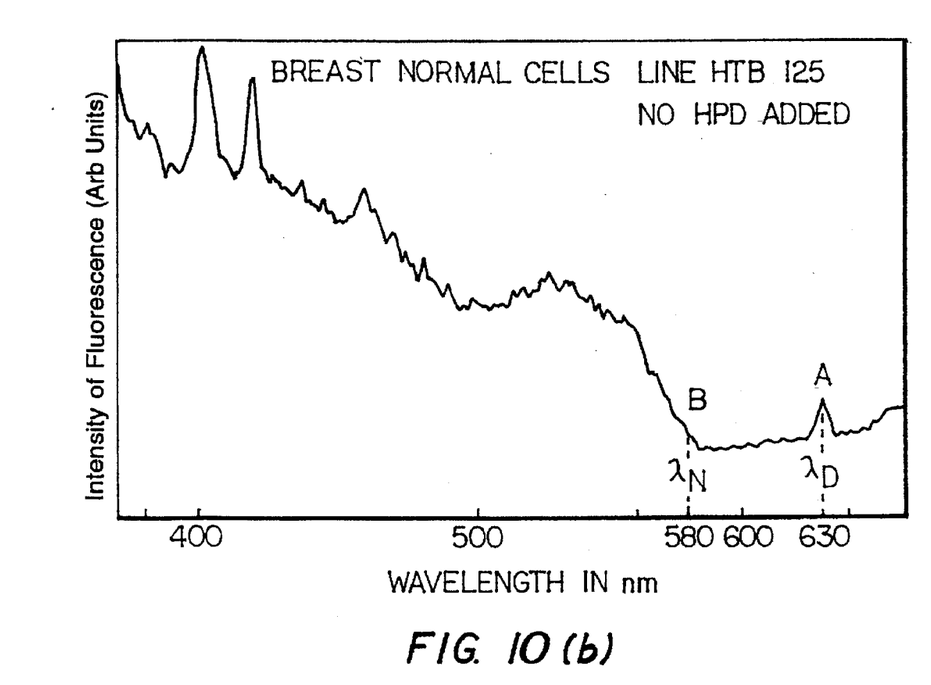
Figure 11A:
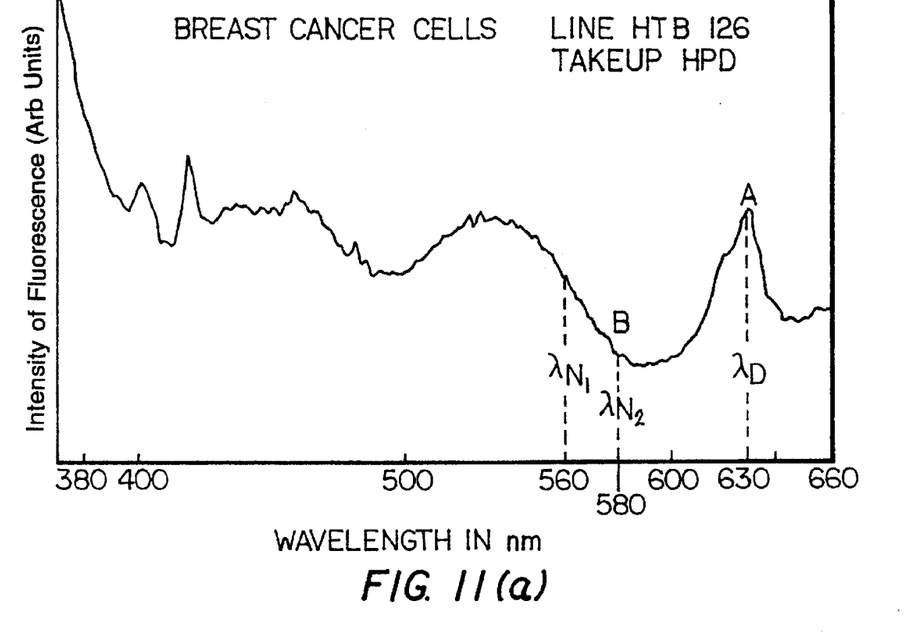
FIGS. 11(a) and 11(b) are the fluorescence emission spectra obtained when light at a wavelength of about 350 nm was used to excite malignant cells to which hematoporphyrin derivative either was or was not added, respectively.
Figure 11B:
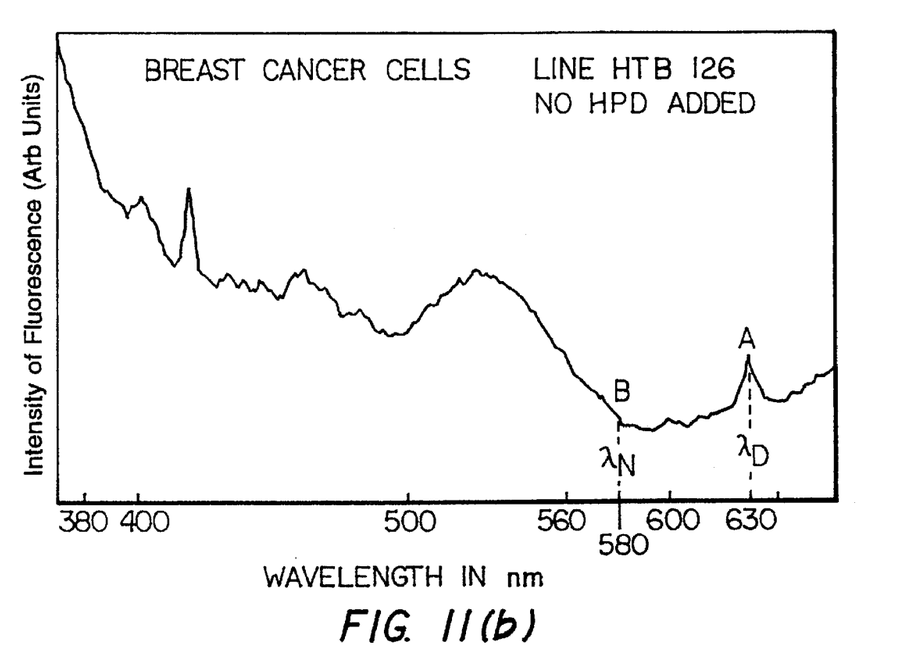

Referring now to FIG. 3, there is shown a third embodiment of a system constructed according to the teachings of the present invention for making a map of an area of a Pap smear-type sample, the system being represented generally by reference numeral 71.

FIGS. 4–9 show schematically how the comparatively greater intensity of fluorescence obtained from malignant cells as compared to non-malignant cells can be used to characterize a cell whose condition is unknown. (Note, in particular, the utility of the discriminator level in this regard.)

EXAMPLES

Cell samples taken from normal cell line HTB 125 and malignant cell line HTB 126 were each placed in a plurality of separate flasks. 3 ml aliquots of HPD at a concentration of $1.0 \times 10^{-3}$ were added to some of the flasks, and the dye was allowed to incubate with the samples for either one half hour or one hour. To wash out the extra dye, 10 ml aliquots of PBS (pH=7.4) were added to the HPD-containing flasks, and the cells were collected by centrifugation two times. The cell samples were then excited at either 350 nm or 380 nm, and the resultant fluorescence was measured at 580 nm and 630 nm. The results of these experiments are seen below in Tables I and II and in FIGS. 10 and 11.

TABLE I

The Fluorescence Intensity of Normal and Cancerous Cells to Which HPD Dye Either Has or Has Not Been Added. Fluorescence Intensity Values Are Read at 630 nm.

| Type of Cell | Cell Line | Int. w/added HPD | Int. w/o HPD | Iw/Iwo |
|---|---|---|---|---|
| Normal | HTB 125 | 1.0 | 0.5 | 2.0 |
| Cancer | HTB 126* | 9.0 | 0.5 | 18.0 |
| Cancer | HTB 126 | 6.0 | 1.0 | 6.0 |
| Cancer | Pap Smear VAK-B/ S.L. | 10.2 | 4.1 | 2.5 |

*excitation at 380 nm

TABLE II

The Ratios of Intensity at Wavelength 630 nm to 580 nm. The Integrated areas are over $\Delta\lambda \approx 20$ nm.

| | | $I_{630 nm}/I_{580 nm}$ | |
|---|---|---|---|
| Type of Cell | Cell Line | HPD Added | No HPD Added |
| Normal | HTB 125 | 2.0 | 1.25 |
| Cancer | HTB 126 | 5.0 | 1.25 |

As can be seen, when HPD is added to the samples, the intensity of fluorescence at 630 nm and the ratio of intensities at 630 nm and 580 nm is markedly different for the normal and the cancerous samples. In contrast, when HPD is not added to the samples, the intensity values for the normal and the cancerous samples are about the same.

Referring to Table I, it should also be noted that $I_W/I_{WO}$, the ratio of intensities at 630 nm for samples to which HPD has and has not been added, is quite different for the normal and cancerous samples. As can be seen, the ratios for the cancer-containing samples are comparatively high (i.e., varying from 2.5 to 18.0) whereas the ratio for the non-cancer containing sample is comparatively low (i.e., 2.0). In fact, it is believed that the ratio for the Pap smear sample VAK-B/S.L. would have been greater than the 2.5 reported were it not for the fact that (1) the cells were not washed after addition of the dye, (2) the cells were dead (as opposed to the living cells in the other samples), (3) there might have been some alignment problems arising from the removal and replacement of the sample in between measurements, (4) measurements were only taken at 630 nm and not at a normalizing wavelength, and (5) the amount of dye added was not controlled.

Figure 12:
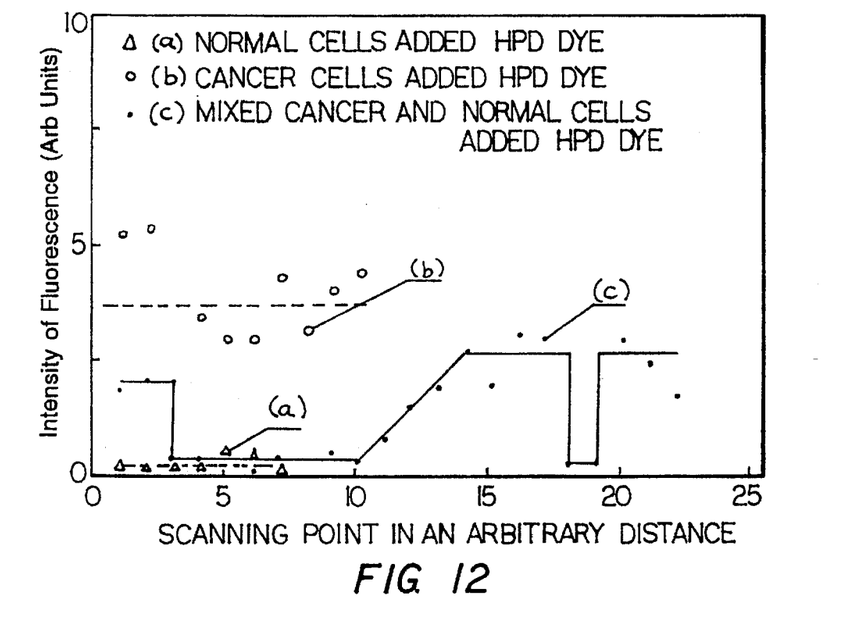
FIG. 12 shows the intensity of fluorescence as a function of scanning point in an arbitrary distance for normal cells, cancer cells, and a mixture of normal and cancer cells, respectively, to which hematoporphyrin derivative has been added.

Referring now to FIG. 12, fluorescence intensity is shown as a function of scanning distance for three groups of cells to which HPD dye was added. Curve (a) corresponds to a group of normal cells, curve (b) corresponds to a group of cancerous cells, and curve (c) corresponds to a mixed group of normal and cancerous cells. The three groups of cells were allowed to incubate with HPD for one hour, were smeared on glass slides, and then scanned using an optical fiber head having an excitation beam diameter of 1 mm and a collection fiber diameter of about 2 mm. As can be seen, the ratio of curve (b) to curve (a) is about 8, and in curve (c), the ratio maximum to minimum is about 3. Both ratio values are in the common region. In curve (c), the ratio value (i.e. about 3) is a little smaller than the ratio value (i.e. approximately 8) of curve (b) to curve (a), which were not exactly the same during measurements. The concentration, thickness, and uniformity of cells in curve (c) may be less than in curves (a) and (b) due to the mixing of cancerous and normal cells. From the left side of curve (c) (i.e., scanning points 3–11), a lower averaged ratio level (i.e., about 0.5) is shown, meaning that the number of normal cells exceeds the number of cancerous cells. At scanning points 12–17, an average ratio level is seen to increase (about 2.5), which means that the number of cancer cells exceeds the number of normal cells. At scanning points 18 and 19, the ratio of less than 0.5 indicates the presence of normal cells, and at scanning points 20–22, the ratio of greater than 2.0 indicates the presence of cancerous cells.

Figure 13:
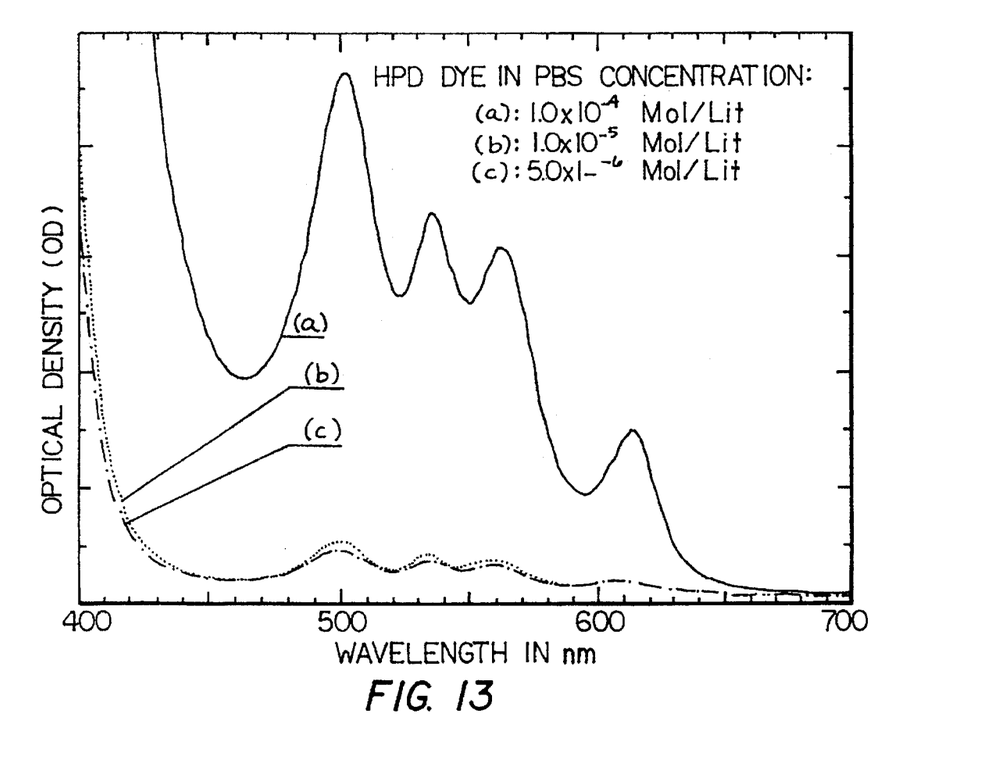
FIG. 13 shows the absorption spectra of hematoporphyrin derivative at different concentrations.
Figure 14:
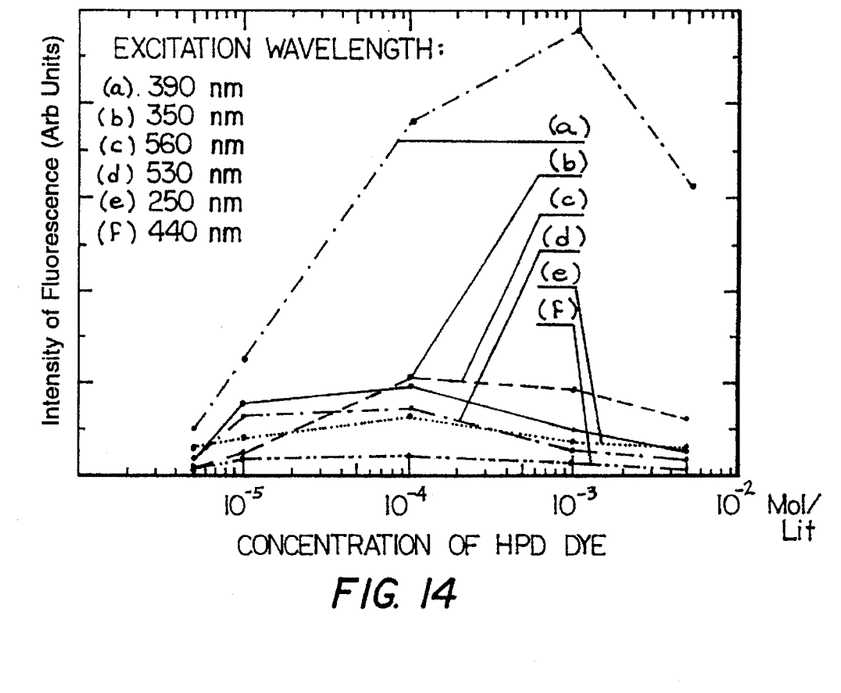
FIG. 14 shows the intensity of fluorescence of hematoporphyrin derivative as a function of concentration at various excitation wavelengths.

Referring now to FIGS. 13 and 14, the absorption spectra of HPD as a function of concentration and the fluorescence emission spectra at 610 nm for different concentrations of HPD and at various excitation wavelengths are shown, respectively. As can be seen therefrom, the optimum excitation wavelength is about 390 nm and the optimum concentration of HPD is approximately $1.0 \times 10^{-3}$ Mol/L.

Figure 15:
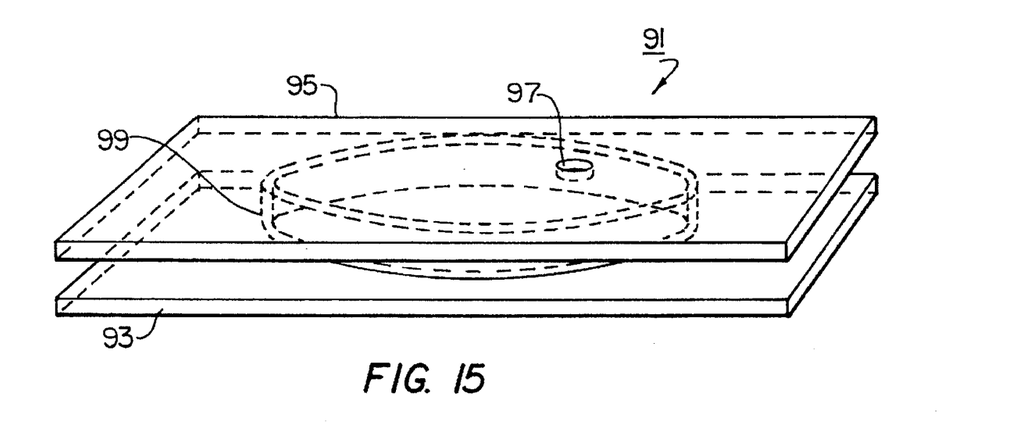
FIG. 15 is a perspective view of a cuvette constructed according to the teachings of the present invention for holding a Pap smear-type sample.

As can readily be appreciated, when using the technique of the present invention to distinguish malignant cells from non-malignant cells in Pap smear-type samples, it is rather important that the sample be spread thinly and uniformly to minimize the occurrence of false positive readings attributable to the cumulative fluorescence of a stack of non-malignant cells. Referring now to FIG. 15, there is illustrated a cuvette 91 for holding a Pap smear-type sample, the cuvette being designed to address the problems discussed above. As can be seen, cuvette 91 includes a pair of optical glass plates 93 and 95. The top plate 95 has a hole 97 through which the sample may be inserted. Cuvette 91 also includes a ring 99 of flexible thickness which is disposed between plates 95 and 97. Ring 99 retains the sample and ensures that the sample has a uniform thickness.

It is expected that fluorescent dyes which preferentially stain malignant cells as opposed to non-malignant cells will also preferentially stain pre-malignant cells as opposed to non-malignant cells (albeit possibly not quite to the extent that they preferentially stain malignant cells as opposed to non-malignant cells). Consequently, it is envisioned that the teachings of the present invention as set forth above can be extended to distinguishing pre-malignant cells from non-malignant cells; accordingly, for purposes of the present invention, terms such as "malignant" and "cancerous" should be considered as including "pre-malignant" or other similar states.

The embodiments of the present invention are intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. A method of examining the cells present within an area of a Pap smear for purposes of detecting cancer, the method comprising the steps of:
   a) exposing the cells present within the area of the Pap smear to a fluorescent dye which preferentially stains malignant cells as opposed to non-malignant cells;
   b) illuminating the area with light of a wavelength sufficient to cause the fluorescent dye to fluoresce whereby fluorescent light is emitted from the area;
   c) measuring the intensity of fluorescent light emitted from the area as a function of location within the area at a wavelength indicative of fluorescence of the fluorescent dye, said measuring step comprising passing the fluorescent light through a filter selective for said wavelength indicative of fluorescence of said fluorescent dye and then converting the filtered fluorescent light from optical signals into electrical signals corresponding in intensity thereto;
   d) comparing the electrical signals obtained in step (c) to appropriate standards obtained from cells known to be malignant and non-malignant; and
   e) using the results of said comparisons to generate a map of the area, said map conveying the spatial distribution of cells within the area and a characterization of each cell within the area as being either malignant or non-malignant.

2. The method as claimed in claim 1 wherein said fluorescent dye is selected from the group consisting of hematoporphyrin, hematoporphyrin derivative, dihematoporphyrin ether/ester, tetramicin, rhodamine, and cyanine.

3. The method as claimed in claim 2 wherein said fluorescent dye is hematoporphyrin derivative.

4. The method as claimed in claim 2 wherein said fluorescent dye is selected from the group consisting of hematoporphyrin, hematoporphyrin derivative, dihematoporphyrin ether/ester.

5. The method as claimed in claim 4 wherein the fluorescent dye used has an absorption spectrum and wherein said illuminating step comprises illuminating the area with light at a wavelength within the absorption spectrum for the fluorescent dye used.

6. The method as claimed in claim 5 wherein said fluorescent dye is hematoporphyrin and wherein said measuring step comprises measuring the intensity of fluorescence at a wavelength of about 820 nm or about 860 nm.

7. The method as claimed in claim 5 wherein said illuminating step comprises illuminating the area with light having a wavelength between about 300 nm and about 400 nm.

8. The method as claimed in claim 7 wherein said illuminating step comprises illuminating the area with light having a wavelength between about 350 nm and about 400 nm.

9. The method as claimed in claim 5 wherein said fluorescent dye is hematoporphyrin derivative or dihematoporphyrin ether/ester and wherein said measuring step comprises measuring the intensity of fluorescence at a wavelength of about 630 nm or about 690 nm.

10. The method as claimed in claim 9 wherein said fluorescent dye is hematoporphyrin derivative and wherein said measuring step comprises measuring the intensity of fluorescence at a wavelength of about 630 nm.

11. The method as claimed in claim 10 wherein said exposing step comprises adding an appropriate amount of hematoporphyrin derivative to the area and removing any excess hematoporphyrin derivative from the area.

12. The method as claimed in claim 11 wherein the hematoporphyrin derivative added to the cell is in solution at a concentration of approximately $1.0 \times 10^{-3}$ Mol/L.

13. A method of examining the cells present within an area of a Pap smear for purposes of detecting cancer, the method comprising the steps of:

a) exposing the cells within the area of the Pap smear to a fluorescent dye which preferentially stains malignant cells as opposed to non-malignant cells;

b) illuminating the area with light of a wavelength sufficient to cause the fluorescent dye to fluoresce whereby fluorescent light is emitted from the area;

c) measuring the intensity of fluorescent light emitted from the area as a function of location within the area at a reference wavelength and at a wavelength indicative of fluorescence of the fluorescent dye, said measuring step comprising passing the fluorescent light alternately through a filter selective for said wavelength indicative of fluorescence of the fluorescent dye and through a filter selective for said reference wavelength and then converting the filtered fluorescent light from optical signals into electrical signals corresponding in intensity thereto;

d) determining the ratio of intensities of said electrical signals corresponding to the fluorescent light at said reference wavelength and at said wavelength indicative of fluorescence of the fluorescent dye;

e) comparing said ratio to standard ratios obtained from malignant and non-malignant cells; and f) using the results of said comparisons to generate a map of the area, said map conveying the spatial distribution of cells within the area and a characterization of each cell within the area as being either malignant or non-malignant using said comparisons.

14. The method as claimed in claim 13 wherein said fluorescent dye is selected from the group consisting of hematoporphyrin, hematoporphyrin derivative, dihematoporphyrin ether/ester, tetramicin, rhodamine, and cyanine.

15. The method as claimed in claim 13 wherein said fluorescent dye is selected from the group consisting of hematoporphyrin, hematoporphyrin derivative, and dihematoporphyrin ether/ester.

16. The method as claimed in claim 15 wherein the fluorescent dye used has an absorption spectrum and wherein said illuminating step comprises illuminating the area with light at a wavelength within the absorption spectrum for the fluorescent dye used.

17. The method as claimed in claim 16 wherein said illuminating stem comprises illuminating the area with light at a wavelength between about 300 nm and about 400 nm.

18. The method as claimed in claim 17 wherein said illuminating step comprises illuminating the area with light having a wavelength between about 350 nm and about 400 nm.

19. The method as claimed in claim 18 wherein said fluorescent dye is hematoporphyrin derivative, or dihematoporphyrin ether/ester and wherein said measuring step comprises measuring the intensity of fluorescence at a reference wavelength of about 440 nm, about 560 nm, or about 580 nm and at a wavelength indicative of fluorescence of said fluorescent dye of about 630 nm or about 690 nm.

20. The method as claimed in claim 18 wherein said fluorescent dye is hematoporphyrin and wherein said measuring step comprises measuring the intensity of fluorescence from the cell at a reference wavelength of about 440 nm about 560 nm or about 580 nm. at a wavelength at which the fluorescent dye fluoresces of about 620 nm or about 660 nm.

21. A method of making a map of the spatial distribution of cells within an area of a Pap smear and for characterizing each of the cells within the area as being either malignant or non-malignant, the method comprising the steps of:

a) exposing the cells within the area of the Pap smear to a fluorescent dye which preferentially stains malignant cells as opposed to non-malignant cells;

b) illuminating the area with light of a wavelength sufficient to cause the fluorescent dye to fluoresce whereby fluorescent light is emitted from the area;

c) measuring at a wavelength indicative of fluorescence of the fluorescent dye the fluorescence intensity of the entire illuminated area as a function of location therewithin, said measuring step comprising passing the fluorescent light through a filter selective for said wavelength indicative of fluorescence of the fluorescent dye and then converting the filtered fluorescent light from optical signals into electrical signals corresponding in intensity thereto;

d) comparing the electrical signals emitted from each location of the entire illuminated area to standards which permit each location to be characterized as corresponding to a malignant cell, a non-malignant cell or background;

e) characterizing each location on the basis of said comparisons; and f) displaying the results of said characterizations in the form of a map.

22. A method of examining the cells present within an area of a Pap smear for purposes of detecting cancer, the method comprising the steps of:

a) exposing the cells within the area of the Pap smear to a fluorescent dye which preferentially stains malignant cells as opposed to non-malignant cells;

b) illuminating the area with light of a wavelength sufficient to cause the fluorescent dye to fluoresce whereby fluorescent light is emitted from the area;

c) measuring the intensity of fluorescent light emitted from the area as a function of location within the area at a reference wavelength and at a wavelength indicative of fluorescence of the fluorescent dye, said measuring step comprising passing the fluorescent light alternately through a filter selective for said wavelength indicative of fluorescence of the fluorescent dye and through a filter selective for said reference wavelength and then converting the filtered fluorescent light from optical signals into electrical signals corresponding in intensity thereto;

d) determining the difference in intensities of the electrical signals corresponding to the optical signals at said reference wavelength and at said wavelength indicative of fluorescence of the fluorescent dye;

e) comparing said difference to standard differences obtained from malignant and non-malignant cells; and f) using said comparisons to generate a map conveying the spatial distribution of cells within the area and a characterization of each cell within the area as being either malignant or non-malignant.

23. A method of cancer-screening a cell sample containing cells whose cancer condition are unknown, the method comprising the steps of:

a) exposing the cell sample to a fluorescent dye which preferentially stains malignant cells as opposed to non-malignant cells;

b) preparing a monolayer spread with the stained cell sample;

c) illuminating an area of the monolayer spread with light of a wavelength sufficient to cause the fluorescent dye to fluoresce whereby fluorescent light is emitted from the area;

d) measuring the intensity of fluorescent light emitted from the area as a function of location within the area at a wavelength indicative of fluorescence of the fluorescent dye, said measuring step comprising passing the fluorescent light through a filter selective for said wavelength indicative of fluorescent light and then converting the filtered fluorescent light from optical signals into electrical signals corresponding in intensity thereto;

e) comparing the electrical signals obtained in step (d) to appropriate standards obtained from cells known to be malignant and non-malignant; and f) using said comparisons to generate a map conveying the spatial distribution of cells within the area and a characterization of each cell within the area as being either malignant or non-malignant.

24. The method as claimed in claim 23 wherein said illuminating step comprises illuminating the entirety of the area at once.

25. The method as claimed in claim 23 wherein said illuminating step comprises illuminating successive portions of the area.

* * * * *